US011369332B2

(12) United States Patent
Kunieda et al.

(10) Patent No.: US 11,369,332 B2
(45) Date of Patent: Jun. 28, 2022

(54) RADIATION IMAGING APPARATUS AND METHOD OF CONTROLLING THE SAME, AND RADIATION IMAGING SYSTEM

(71) Applicant: CANON KABUSHIKI KAISHA, Tokyo (JP)

(72) Inventors: Shutaro Kunieda, Yokohama (JP); Tomoyuki Yagi, Chofu (JP)

(73) Assignee: CANON KABUSHIKI KAISHA, Tokyo (JP)

(*) Notice: Subject to any disclaimer, the term of this patent is extended or adjusted under 35 U.S.C. 154(b) by 0 days.

(21) Appl. No.: 16/909,728

(22) Filed: Jun. 23, 2020

(65) Prior Publication Data
US 2020/0405254 A1  Dec. 31, 2020

(30) Foreign Application Priority Data

Jun. 26, 2019  (JP) .............................. JP2019-118381

(51) Int. Cl.
*A61B 6/00* (2006.01)

(52) U.S. Cl.
CPC ............ *A61B 6/542* (2013.01); *A61B 6/4233* (2013.01)

(58) Field of Classification Search
CPC ............................... A61B 6/542; A61B 6/4233
See application file for complete search history.

(56) References Cited

U.S. PATENT DOCUMENTS

| 2,985,761 | A | * | 5/1961 | Ohmart | H05G 1/44 378/97 |
| 3,546,461 | A | * | 12/1970 | Craig | G03B 42/02 378/97 |
| 3,792,267 | A | * | 2/1974 | Westerkowsky | H05G 1/44 378/97 |
| 3,911,273 | A | * | 10/1975 | Franke | H05G 1/32 378/97 |
| 4,313,055 | A | * | 1/1982 | Richter | H05G 1/44 378/91 |
| 2004/0228452 | A1 | * | 11/2004 | Rinaldi | A61B 6/145 378/207 |
| 2012/0044392 | A1 | * | 2/2012 | Takenaka | H04N 5/367 348/246 |
| 2012/0049077 | A1 | * | 3/2012 | Okada | H04N 5/32 250/370.08 |
| 2013/0058457 | A1 | * | 3/2013 | Kuwabara | A61B 6/548 378/62 |

(Continued)

FOREIGN PATENT DOCUMENTS

JP  2012-52896 A  3/2012
JP  2014-90869 A  5/2014

*Primary Examiner* — Blake C Riddick
(74) *Attorney, Agent, or Firm* — Canon U.S.A., Inc. IP Division

(57) ABSTRACT

Provided is a system capable of preventing inappropriate radiation stop control from being performed. A radiation imaging apparatus configured to perform imaging by radiation includes: an imaging unit including a dose signal output pixel arranged to output an electric signal based on a dose of the radiation that has entered the dose signal output pixel; and a processing unit configured to perform processing of comparing an integration value of the electric signal output from the dose signal output pixel included in the imaging unit to a threshold value during a period in which the radiation is not applied to the imaging unit.

19 Claims, 11 Drawing Sheets

(56) References Cited

U.S. PATENT DOCUMENTS

| | | | | |
|---|---|---|---|---|
| 2013/0077744 A1* | 3/2013 | Kamiya | .................. | A61B 6/548 |
| | | | | 378/62 |
| 2013/0121464 A1* | 5/2013 | Tajima | .................. | A61B 6/4283 |
| | | | | 378/62 |
| 2013/0148782 A1* | 6/2013 | Tajima | .................. | A61B 6/4233 |
| | | | | 378/62 |
| 2013/0202086 A1* | 8/2013 | Tsuji | ..................... | H01L 27/144 |
| | | | | 378/62 |
| 2013/0208852 A1* | 8/2013 | Koishi | ................... | A61B 6/548 |
| | | | | 378/19 |
| 2013/0223592 A1* | 8/2013 | Sato | ..................... | A61B 6/4233 |
| | | | | 378/62 |
| 2014/0086391 A1* | 3/2014 | Ohta | .................... | H04N 5/2351 |
| | | | | 378/91 |
| 2014/0205066 A1* | 7/2014 | Kitagawa | ................ | A61B 6/542 |
| | | | | 378/62 |
| 2014/0239187 A1* | 8/2014 | Iwashita | .............. | H04N 5/3575 |
| | | | | 250/394 |
| 2015/0055753 A1* | 2/2015 | Tajima | .................... | A61B 6/08 |
| | | | | 378/62 |
| 2015/0153464 A1* | 6/2015 | Imamura | ........... | H01L 27/14605 |
| | | | | 378/207 |
| 2015/0351715 A1* | 12/2015 | Ota | ........................ | A61B 6/54 |
| | | | | 378/64 |
| 2016/0134818 A1* | 5/2016 | Iwashita | ................ | A61B 6/585 |
| | | | | 348/162 |
| 2018/0031714 A1* | 2/2018 | Tajima | ................. | A61B 6/4266 |

* cited by examiner

RADIATION IMAGING APPARATUS AND METHOD OF CONTROLLING THE SAME, AND RADIATION IMAGING SYSTEM

BACKGROUND

Field of the Disclosure

The present disclosure relates to a radiation imaging apparatus configured to perform imaging by radiation and a method of controlling the same, and to a radiation imaging system including the radiation imaging apparatus.

Description of the Related Art

Radiation imaging apparatus including an imaging unit, for example, a sensor panel configured to detect X rays or other such radiations are widely used in the fields of industry, medicine, and the like. In recent years, there have been investigated portable radiation imaging apparatus capable of performing imaging in a plurality of imaging modes suited to purposes, which include a mode of capturing a still image and a mode of capturing a moving image. There have also been investigated radiation imaging apparatus capable of performing automatic exposure control (AEC) by detecting an integrated application amount of a radiation that has passed through a subject to be examined and stopping the irradiation of the radiation by a radiation source when the integrated application amount has reached a proper amount.

In Japanese Patent Application Laid-Open No. 2012-52896, there is disclosed an example of a radiographic imaging apparatus capable of suppressing the effect of noise to accurately detect a radiation even when noise occurs due to an external disturbance or the like by detecting a radiation based on a difference between an electric signal that corresponds to charges generated at a sensor portion for radiation detection and flows through a first line and an electric signal flowing through a second line having a substantially same wiring pattern as that of the first line. Further, in Japanese Patent Application Laid-Open No 2014-090869, there is disclosed an example of a radiation imaging system configured to convert, when occurrence of disturbance noise is detected in a signal representing a dose of radiation by detection means, the signal into a signal representing a dose of radiation smaller than the dose of radiation represented by the signal, to thereby accurately perform radiation stop control even when noise occurs to eliminate the need to perform imaging again due to the lack of the radiation dose.

However, in the related art including Japanese Patent Application Laid-Open No 2014-090869, for example, inappropriate radiation stop control may be performed due to, for example, a failure of a device configured to detect the dose of radiation, which is caused by an aging deterioration of the device, an impact against the device, or the like.

SUMMARY

At least one embodiment of the present invention has been made in view of the above-mentioned problem, and has an object to provide a system capable of preventing inappropriate radiation stop control from being performed.

According to at least one aspect of the present invention, there is provided a radiation imaging apparatus configured to perform imaging by radiation, the radiation imaging apparatus including: an imaging unit including a dose signal output pixel arranged to output an electric signal based on a dose of the radiation that has entered the dose signal output pixel; and a processing unit configured to perform processing of comparing an integration value of the electric signal output from the dose signal output pixel to a threshold value during a period in which the radiation is not applied to the imaging unit.

Further, another aspect of the present invention includes a method of controlling the above-mentioned radiation imaging apparatus and a radiation imaging system including the above-mentioned radiation imaging apparatus.

Further features of the present invention will become apparent from the following description of exemplary embodiments with reference to the attached drawings.

DESCRIPTION OF THE EMBODIMENTS

Preferred embodiments of the present invention will now be described in detail in accordance with the accompanying drawings. In the embodiments of the present invention described below, a radiation includes α rays, β rays, and γ rays, which are beams formed by particles (including photons) released by a radioactive decay, and also include, for example, X rays, particle rays, and cosmic rays, which are beams having the same level or more of energy.

First Embodiment

First, a first embodiment of the present invention is described.

Figure 1:
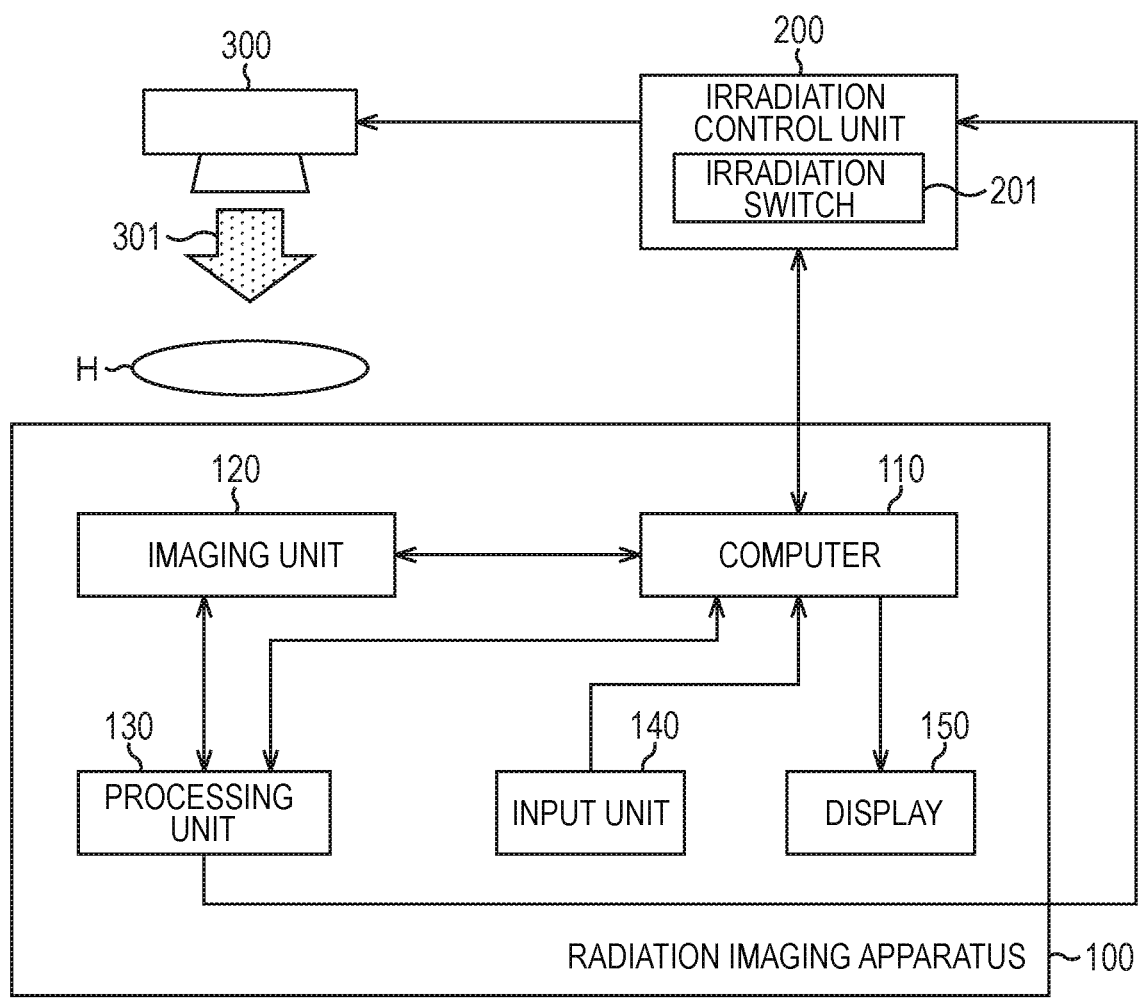
FIG. 1 is a diagram for illustrating an example of a schematic configuration of a radiation imaging system including a radiation imaging apparatus according to a first embodiment of the present invention.

FIG. 1 is a diagram for illustrating an example of a schematic configuration of a radiation imaging system 10 including a radiation imaging apparatus 100 according to the first embodiment of the present invention. As illustrated in FIG. 1, the radiation imaging system 10 includes the radiation imaging apparatus 100, an irradiation control unit 200, and a radiation source 300. The radiation imaging system 10 is configured to electrically capture an image of a subject H to be examined, which is formed by a radiation 301, to obtain an electric radiation image.

The radiation source 300 is configured to perform irradiation of the radiation 301 in accordance with an irradiation permission instruction issued from the irradiation control unit 200. The radiation 301 emitted from the radiation source 300 passes through the subject H to be examined to enter the radiation imaging apparatus 100. Further, the radiation source 300 is configured to stop the irradiation of the radiation 301 in accordance with an irradiation stop instruction issued from the irradiation control unit 200.

The irradiation control unit 200 is configured to control the application of the radiation 301 by the radiation source 300. The irradiation control unit 200 may include an irradiation switch 201. For example, the irradiation control unit 200 controls the application of the radiation 301 by the radiation source 300 based on an operation state of the irradiation switch 201 and various types of instruction information issued from the radiation imaging apparatus 100.

The radiation imaging apparatus 100 is an apparatus configured to capture an image of the subject H to be examined through use of the radiation 301. The radiation imaging apparatus 100 has an automatic exposure control function (AEC function) of controlling stop of application of the radiation 301. As illustrated in FIG. 1, the radiation imaging apparatus 100 includes a computer 110, an imaging unit 120, a processing unit 130, an input unit 140, and a display 150.

The radiation 301 emitted from the radiation source 300 (including the radiation 301 that has passed through the subject H to be examined) enters the imaging unit 120. The imaging unit 120 includes a plurality of image signal output pixels each arranged to output an image signal relating to a radiation image, and a plurality of dose signal output pixels each arranged to output a dose signal being an electric signal that is based on a dose of the applied radiation 301 that has entered the pixel. In the first embodiment, an example in which the pixel is applied as a configuration for outputting the dose signal is described, but a dedicated sensor, for example, may be applied as the configuration.

The processing unit 130 is configured to perform various types of processing relating to the radiation stop control. In the first embodiment, the processing unit 130 performs processing of comparing, during a period in which the radiation 301 is not applied to the imaging unit 120 from the radiation source 300, an integration value of electric signals (dose signals) output from the dose signal output pixels of the imaging unit 120 to a threshold value. After that, in the first embodiment, when the integration value exceeds the threshold value, the processing unit 130 transmits to the irradiation control unit 200 prohibition instruction information for prohibiting the application of the radiation 301 from the radiation source 300 to the imaging unit 120. Then, when receiving the prohibition instruction information from the processing unit 130, the irradiation control unit 200 transmits an irradiation prohibition instruction to the radiation source 300 to control the radiation source 300 so as to prevent the radiation 301 from being applied from the radiation source 300. Meanwhile, in the first embodiment, when the above-mentioned integration value does not exceed the threshold value, the processing unit 130 transmits to the irradiation control unit 200 permission instruction information for permitting the application of the radiation 301 from the radiation source 300 to the imaging unit 120. Then, when receiving the permission instruction information from the processing unit 130, the irradiation control unit 200 transmits an irradiation permission instruction to the radiation source 300 so that the radiation 301 is applied from the radiation source 300.

The processing unit 130 may be formed of, for example, a field programmable gate array (FPGA), an application specific integrated circuit (ASIC), or a general-purpose computer having a program built therein. Further, the processing unit 130 may be formed of all of those devices or a combination of part of those devices.

The computer 110 is configured to perform overall control of the operation of the radiation imaging apparatus 100 and to perform various types of processing. The computer 110 is also configured to communicate to and from the irradiation control unit 200. The computer 110 is further configured to perform processing of, for example, processing the image signal output from the image signal output pixel of the imaging unit 120 to generate radiation image data.

The input unit 140 is configured to input various types of information to the computer 110.

The display 150 is configured to display various types of information and various types of images under the control of the computer 110. For example, when the processing unit 130 has transmitted the prohibition instruction information to the irradiation control unit 200, the display 150 displays an alert indicating the prohibition. Further, for example, the display 150 displays a radiation image that is based on the radiation image data generated by the computer 110.

Figure 2:
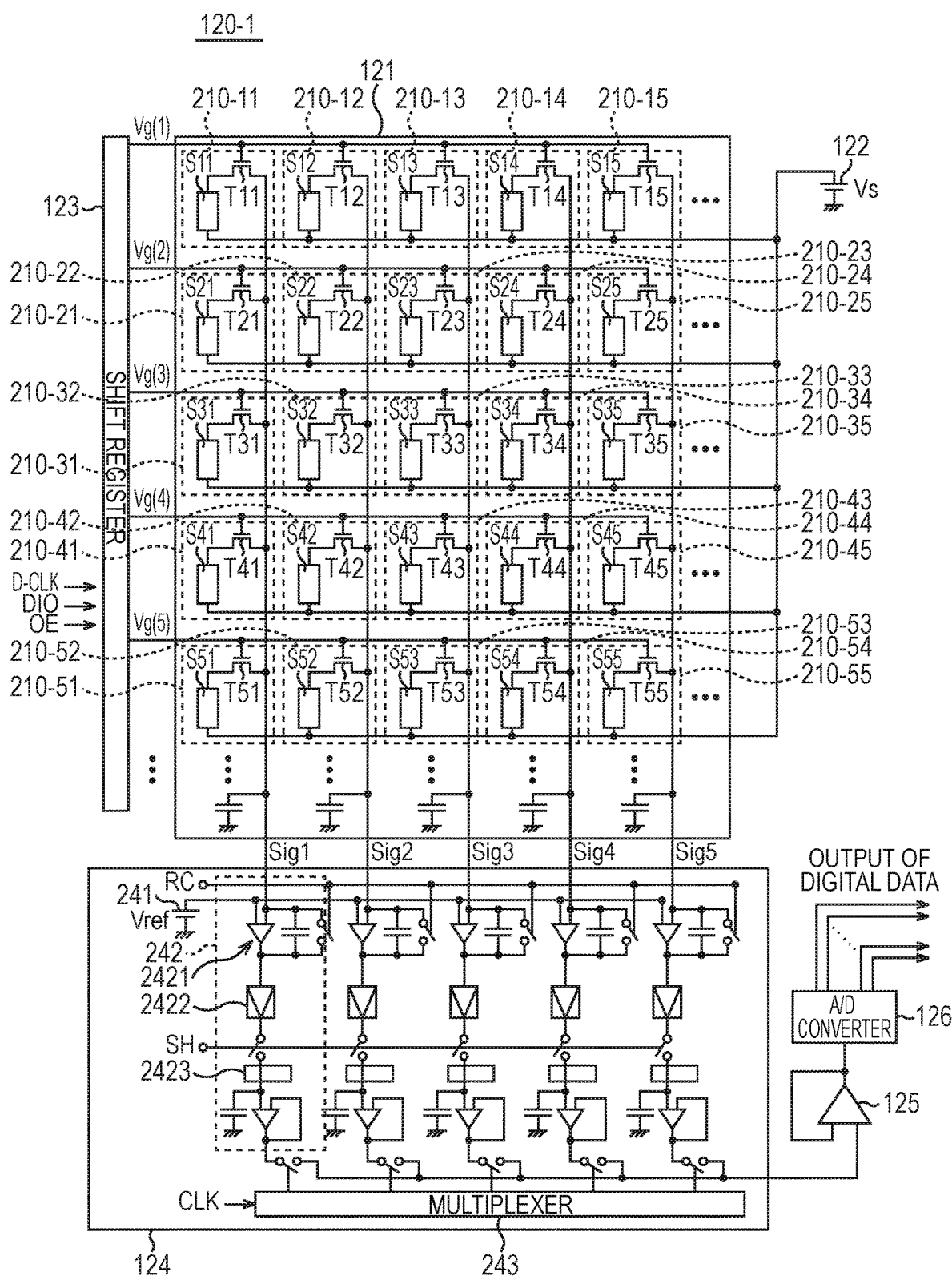
FIG. 2 is a diagram for illustrating an example of an internal configuration of an imaging unit illustrated in FIG. 1.

Next, an internal configuration of the imaging unit 120 illustrated in FIG. 1 is described. FIG. 2 is an illustration of the first embodiment of the present invention, and is a diagram for illustrating an example of the internal configuration of the imaging unit 120 illustrated in FIG. 1. The imaging unit 120 in the first embodiment illustrated in FIG. 2 is hereinafter referred to as "imaging unit 120-1".

As illustrated in FIG. 2, the imaging unit 120-1 includes a pixel region 121, a bias power supply 122, a shift register 123 being a drive circuit, a readout circuit 124, a buffer amplifier 125, and an A/D converter 126.

The pixel region 121 includes, for example, a plurality of pixels 210 arranged in matrix on an insulating substrate. In the example illustrated in FIG. 2, in order to simply the description, there is illustrated the pixel region 121 in which five rows and five columns of pixels 210 (specifically, a pixel 210-11 to a pixel 210-55 illustrated in FIG. 2) are arranged, but in the actual pixel region 121, a larger number of pixels 210 are arranged. For example, in a 17-inch FPD, the pixel region 121 may include about 2,800 rows and about 2,800 columns of pixels 210.

Each pixel 210 includes a conversion element S arranged to convert the radiation 301 that has entered the pixel into electric charges and a switching element T for outputting an electric signal that is based on the electric charges generated by the conversion element S. In the example illustrated in FIG. 2, a conversion element S included in the pixel 210-11 of the first row and the first column is illustrated as "conversion element S11", and a switching element T included in the pixel 210-11 of the first row and the first column is illustrated as "switching element T11". When this example is generalized through use of any natural numbers "m" and "n" to describe the example illustrated in FIG. 2, a conversion element S included in a pixel 210-mn of an m-th row and an n-th column is illustrated as "conversion element Smn", and a switching element T included in the pixel 210-mn of the m-th row and the n-th column is illustrated as "switching element Tmn".

In the first embodiment, an indirect conversion element may be used as the conversion element S. The indirect conversion element includes, for example, a wavelength converter (for example, a scintillator) configured to convert the radiation 301 into light that can be detected by a photoelectric conversion element and the photoelectric conversion element configured to convert the light obtained by the conversion by the wavelength converter into electric charges. In this case, as the photoelectric conversion element, a photodiode having an MIS structure may be used, which is mounted on an insulating substrate, for example, a glass substrate, and has amorphous silicon, for example, as its main material. As another example, as the photoelectric conversion element, a photodiode having a PIN structure may be used, which is mounted on a semiconductor substrate, for example, a silicon substrate. Further, the conversion element S is not limited to the above-mentioned indirect conversion element, and a direct conversion element configured to directly convert the radiation 301 into electric charges may also be used. In this case, amorphous selenium, for example, may be used as the main material of the conversion element. The plurality of conversion elements S illustrated in FIG. 2 detect a two-dimensional distribution of the radiation 301 that has reached the imaging unit 120-1.

As the switching element T, for example, a transistor including a control terminal and two main terminals may be used. In the first embodiment, a thin-film transistor (TFT) may be used as the switching element T.

One of the electrodes of the conversion element S is electrically connected to one of the two main terminals of the switching element T, and the other one of the electrodes of the conversion element S is electrically connected to the bias power supply 122 via a common bias wiring. The switching elements T arranged in the row direction (lateral direction of FIG. 2), for example, the switching elements T11 to T15 of the first row, each have the control terminal electrically connected in common to a drive wiring Vg(1). To the switching elements T11 to T15, a drive signal for controlling a conductive state of the switching elements T11 to T15 is supplied from the shift register 123 via the drive wiring Vg(1). Further, the switching elements T arranged in the column direction (longitudinal direction of FIG. 2), for example, the switching elements T11 to T51 of the first column, each have the other one of the main terminals electrically connected to a signal wiring Sig1. While the switching elements T11 to T51 are in the conductive state, a signal that depends on the electric charges accumulated in the conversion element S is output to the readout circuit 124 via the signal wiring Sig1. The signal wirings Sig1 to Sig5 arranged in the column direction transmit signals output from the pixels 210 connected to the same drive wiring Vg in parallel to the readout circuit 124.

In the first embodiment illustrated in FIG. 2, there may be adopted a mode in which the above-mentioned dose signal output pixel and image signal output pixel included in the imaging unit 120 are formed as the same pixel 210 in the pixel region 121 of the imaging unit 120-1. In this case, the computer 110 of FIG. 1 controls the shift register 123 to vary a timing to drive each pixel 210 from one another, to thereby cause the pixel to function as the dose signal output pixel or the image signal output pixel. For example, the computer 110 of FIG. 1 may select, based on information from the input unit 140, any one of drive modes including a first drive mode of causing the pixel 210 to function as the dose signal output pixel and a second drive mode of causing the pixel 210 to function as the image signal output pixel. Although the mode in which the computer 110 of FIG. 1 performs various types of control of the internal configuration of the imaging unit 120 is described here, the first embodiment is not limited to this mode. A mode in which the processing unit 130 of FIG. 1 performs the above-mentioned control is also applicable to the first embodiment.

The shift register 123 is configured to output, to each drive wiring Vg, based on control signals D-CLK, DIO, and OE supplied from the computer 110 of FIG. 1, a drive signal including a conductive voltage Vcom for setting the switching element T to the conductive state and a non-conductive voltage Vss for setting the switching element T to a non-conducive state. In this manner, the shift register 123 controls the conductive state and the non-conducive state of the switching element T to drive each pixel 210 of the pixel region 121. Specifically, the control signal D-CLK is a shift clock signal of the shift register 123 to be used as the drive circuit. Further, the control signal DIO is a pulse signal to be transferred by the shift register 123. Further, the control signal OE is a signal for controlling an output end of the shift register 123. In the manner described above, a period of time required for driving and a scanning direction are set.

In the readout circuit 124, amplifier circuits 242 configured to amplify signals output in parallel from the pixels 210 arranged in the pixel region 121 are arranged for the respective signal wirings Sig. The amplifier circuit 242 includes an integration amplifier 2421, a variable amplifier 2422, and a sample-and-hold circuit 2423. The integration amplifier 2421 is arranged to amplify the signal output from the pixel 210. More specifically, the integration amplifier 2421 includes an operational amplifier arranged to amplify an electric signal read out from the pixel 210 to output the amplified signal, an integration capacitor, and a reset switch. The integration amplifier 2421 is able to change its amplification factor by changing the value of the integration capacitor. Further, a signal output from the pixel 210 is input to an inverting input terminal of the operational amplifier of the integration amplifier 2421, and a reference voltage Vref is input to a non-inverting input terminal of the operational amplifier from a reference power supply 241. Further, the amplified signal is output from an output terminal of the operational amplifier of the integration amplifier 2421. Further, in the integration amplifier 2421, the integration capacitor is arranged between the inverting input terminal of the operational amplifier and the output terminal thereof. The variable amplifier 2422 is arranged to amplify the signal output from the integration amplifier 2421. The sample-and-hold circuit 2423 is arranged to sample and hold the signal amplified by the integration amplifier 2421 and the variable amplifier 2422. The sample-and-hold circuit 2423 includes a sampling switch and a sampling capacitor. Further, the readout circuit 124 includes a multiplexer 243 arranged to sequentially output signals read out in parallel from the amplifier circuits 242 to output the signal as a serial electric signal.

In the readout circuit 124, operations of respective components are controlled based on control signals RC, SH, and CLK supplied from the computer 110 of FIG. 1. Specifically, the control signal RC is a signal for controlling the operation of the reset switch of the integration amplifier 2421. Further, the control signal SH is a signal for controlling the operation of the sample-and-hold circuit 2423. Further, the control signal CLK is a signal for controlling the operation of the multiplexer 243.

The buffer amplifier 125 is arranged to subject the electric signal output from the multiplexer 243 to impedance conversion to output a resultant signal to the A/D converter 126.

The A/D converter 126 is arranged to convert an analog electric signal output from the buffer amplifier 125 into a digital electric signal. For example, in the drive mode of causing one or a plurality of rows of the pixels 210 of the pixel region 121 as the dose signal output pixels, before or during the irradiation of the radiation 301, a digital electric signal (dose signal) output from the pixel 210 (dose signal output pixel) via the A/D converter 126 is supplied to the processing unit 130 of FIG. 1, for example. Further, for example, in the drive mode of causing a pixel 210 of the pixel region 121 as the image signal output pixel, after the irradiation of the radiation 301, a digital electric signal (image signal) output from the pixel 210 (image signal output pixel) via the A/D converter 126 is supplied to the computer 110 of FIG. 1, for example.

Next, the operation to be performed when, for example, a user operates (turns on) the irradiation switch 201 and thus the irradiation control unit 200 issues a request to perform the irradiation of the radiation 301 to the radiation imaging apparatus 100 is described with reference to FIG. 3 and FIG. 4.

Figure 3:
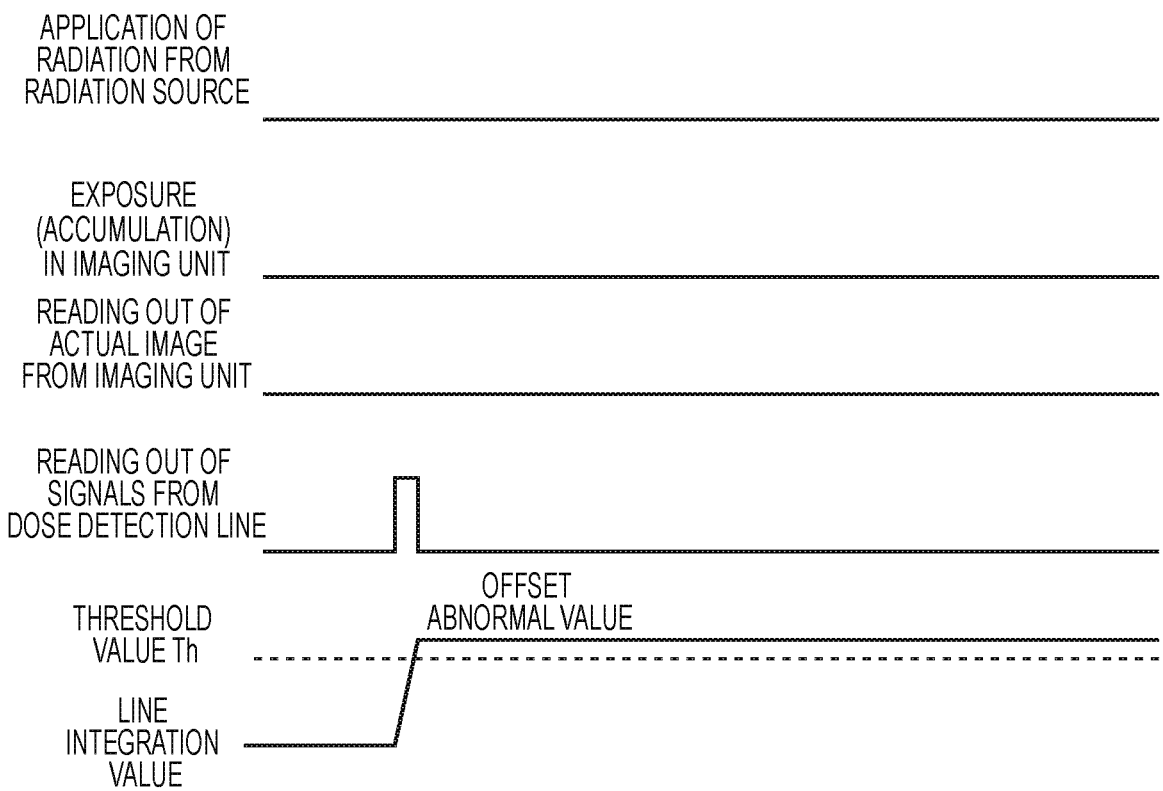
FIG. 3 is a timing chart for illustrating an example of a processing procedure involved in a method of controlling the radiation imaging system including the radiation imaging apparatus according to the first embodiment.

FIG. 3 is a timing chart for illustrating an example of a processing procedure involved in a method of controlling the radiation imaging system 10 including the radiation imaging apparatus 100 according to the first embodiment of the present invention. Specifically, in FIG. 3, there are illustrated, in order from the top, a timing to perform irradiation of the radiation 301 from the radiation source 300, a timing of exposure (accumulation) in the imaging unit 120, a timing to read out an actual image (radiation image) from the imaging unit 120, a timing to read out signals from the dose detection line of the imaging unit 120, the threshold value Th, and a timing at which the integration value of the dose detection line varies. In this case, the timing to read out the actual image (radiation image) from the imaging unit 120 is, for example, in the drive mode of causing the pixel 210 of the pixel region 121 as the image signal output pixel, a timing to read out the electric signal (image signal) from the pixel 210 (image signal output pixel). Further, the timing to read out signals from the dose detection line of the imaging unit 120 is, for example, in the drive mode of causing one or a plurality of rows of the pixels 210 of the pixel region 121 as the dose signal output pixels, a timing to read out the electric signals (dose signals) from the dose signal output pixel line.

In FIG. 3, there is illustrated an example of the operation of the radiation imaging apparatus 100 according to the first embodiment to be performed during the period in which the radiation 301 is not applied to the imaging unit 120 from the radiation source 300. Specifically, in FIG. 3, for example, there is illustrated an operation of reading out the electric signals (dose signals) from the dose signal output pixel line (dose detection line) in the drive mode of causing one or a plurality of rows of the pixels 210 of the pixel region 121 as the dose signal output pixels. Then, in FIG. 3, the processing unit 130 performs processing of comparing the integration value obtained by integrating the read electric signals (dose signals) to the threshold value Th. In the case of FIG. 3, the integration value of the electric signals of the dose detection line (dose signal output pixel line) exceeds the threshold value Th, and hence the processing unit 130 consequently transmits to the irradiation control unit 200 the prohibition instruction information for prohibiting the irradiation of the radiation 301 to the imaging unit 120 from the radiation source 300. When the integration value of the electric signal of the dose detection line (dose signal output pixel line) exceeds the threshold value Th as in the example illustrated in FIG. 3, it is conceivable that an abnormal output of the dose detection line (dose signal output pixel line) occurs due to, for example, a failure caused by an aging deterioration of the dose detection line, an impact against the dose detection line, or the like.

Figure 4:
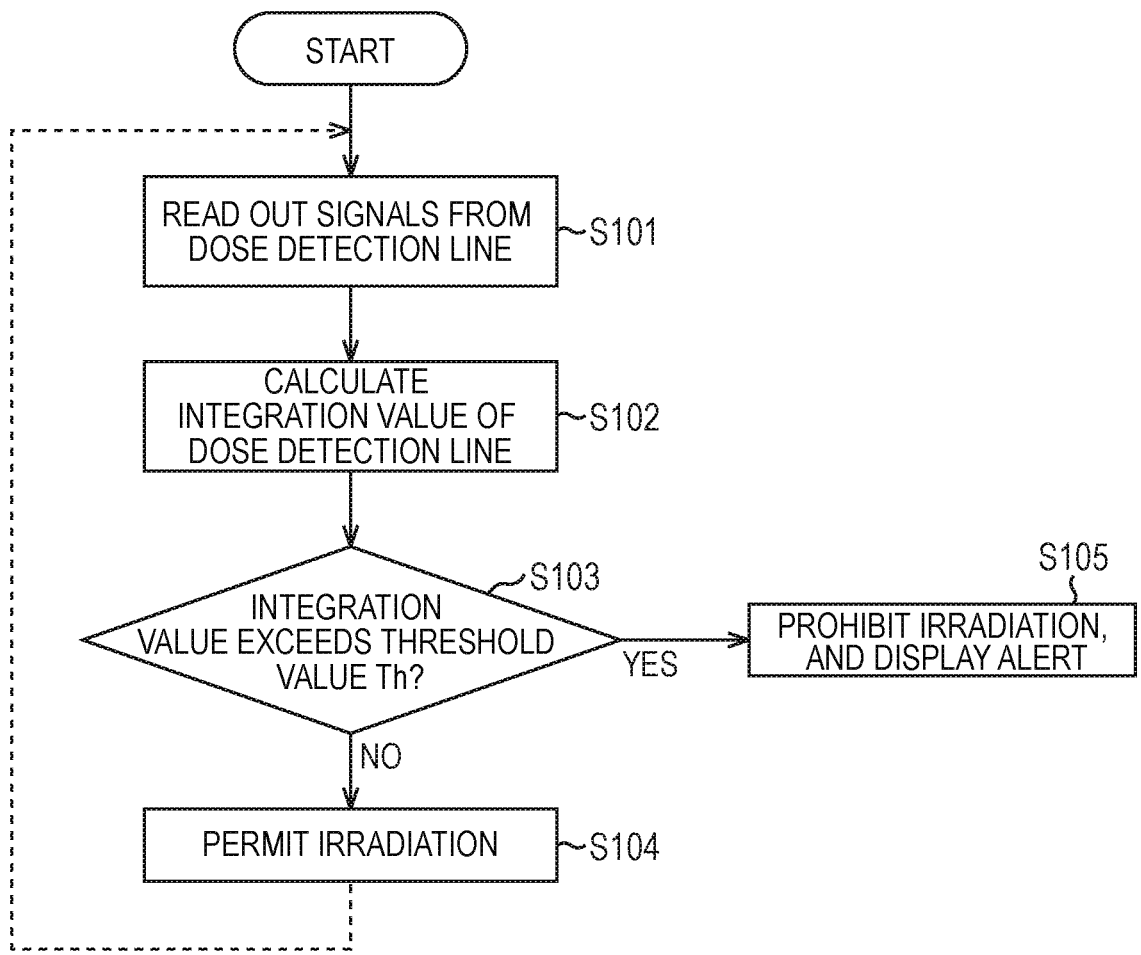
FIG. 4 is a flowchart for illustrating an example of a processing procedure involved in a method of controlling the radiation imaging apparatus according to the first embodiment.

FIG. 4 is a flowchart for illustrating an example of a processing procedure included in a method of controlling the radiation imaging apparatus 100 according to the first embodiment of the present invention. The flowchart illustrated in FIG. 4 is started under a state in which the radiation 301 is not applied to the imaging unit 120 from the radiation source 300 (under a state before the irradiation of the radiation 301).

First, in Step S101, for example, in the drive mode of causing one or a plurality of rows of the pixels 210 of the pixel region 121 to function as the dose signal output pixel, the processing unit 130 reads out electric signals (dose signals) from the dose signal output pixel line (dose detection line).

Subsequently, in Step S102, the processing unit 130 integrates the electric signals (dose signals) read out in Step S101 from the dose signal output pixel line to calculate an integration value of the electric signals.

Subsequently, in Step S103, the processing unit 130 compares the integration value calculated in Step S102 to the threshold value Th, and determines whether or not the integration value calculated in Step S102 exceeds the threshold value Th.

As a result of the determination of Step S103, when the integration value calculated in Step S102 does not exceed the threshold value Th (Step S103: NO), the processing proceeds to Step S104. When the processing proceeds to Step S104, the processing unit 130 determines, for example, that an abnormal output of the dose signal output pixel line does not occur, and transmits to the irradiation control unit 200 the permission instruction information for permitting the irradiation of the radiation 301 to the imaging unit 120 from the radiation source 300. Then, when receiving the permission instruction information from the processing unit 130, the irradiation control unit 200 transmits the irradiation permission instruction to the radiation source 300 to control the radiation source 300 such that the radiation 301 is applied from the radiation source 300. After that, when the processing of Step S104 is finished, the processing of the flowchart of FIG. 4 may be brought to an end, or the processing may return to Step S101 so that the processing of Step S101 and the subsequent steps may be performed again.

Meanwhile, as a result of the determination of Step S103, when the integration value calculated in Step S102 exceeds the threshold value Th (Step S103: YES), the processing proceeds to Step S105. When the processing proceeds to Step S105, the processing unit 130 determines, for example, that an abnormal output of the dose signal output pixel line occurs, and transmits to the irradiation control unit 200 the prohibition instruction information for prohibiting the irradiation of the radiation 301 to the imaging unit 120 from the radiation source 300. Then, when receiving the prohibition instruction information from the processing unit 130, the irradiation control unit 200 transmits the irradiation prohibition instruction to the radiation source 300 to control the radiation source 300 so as to prevent the radiation 301 from being applied from the radiation source 300. Further, for example, the abnormal output of the dose signal output pixel line occurs, and hence there is a possibility that appropriate radiation stop control cannot be performed. Thus, in Step S105, alert indicating that, for example, appropriate dose detection cannot be performed is displayed on the display 150. This allows the user to grasp the fact that appropriate radiation stop control cannot be performed because a dose of the radiation cannot appropriately be detected.

In the radiation imaging apparatus 100 according to the first embodiment, the processing unit 130 is configured to compare, during the period in which the radiation 301 is not applied to the imaging unit 120, the integration value of the electric signals output from the dose signal output pixel line (dose detection line) to the threshold value Th. According to this configuration, when the integration value of the electric signals output from the dose signal output pixel line exceeds the threshold value Th, the processing unit 130 can determine, for example, that an abnormal output of the dose signal output pixel line occurs, and can transmit to the irradiation control unit 200 the prohibition instruction information for prohibiting the irradiation of the radiation 301 to the imaging unit 120 from the radiation source 300. With this configuration, it is possible to prevent inappropriate radiation stop control from being performed. It is also possible to prevent unnecessary radiation imaging.

Second Embodiment

Next, a second embodiment of the present invention is described. In the following description of the second embodiment, a description of matters common to the first embodiment described above is omitted, and matters different from those of the first embodiment described above are described.

A schematic configuration of a radiation imaging system including a radiation imaging apparatus according to the second embodiment is the same as the schematic configuration of the radiation imaging system 10 of the radiation imaging apparatus 100 according to the first embodiment, which is illustrated in FIG. 1. Further, an internal configuration of an imaging unit 120 of the radiation imaging apparatus 100 according to the second embodiment is the same as the internal configuration of the imaging unit 120-1 in the first embodiment, which is illustrated in FIG. 2.

Specifically, the second embodiment is an embodiment mode relating to various modes after the irradiation of the radiation 301 is permitted in Step S104 of FIG. 4. The radiation imaging apparatus 100 according to the second embodiment has an automatic exposure control function (AEC function) of controlling the stop of the irradiation of the radiation 301.

Figure 5:
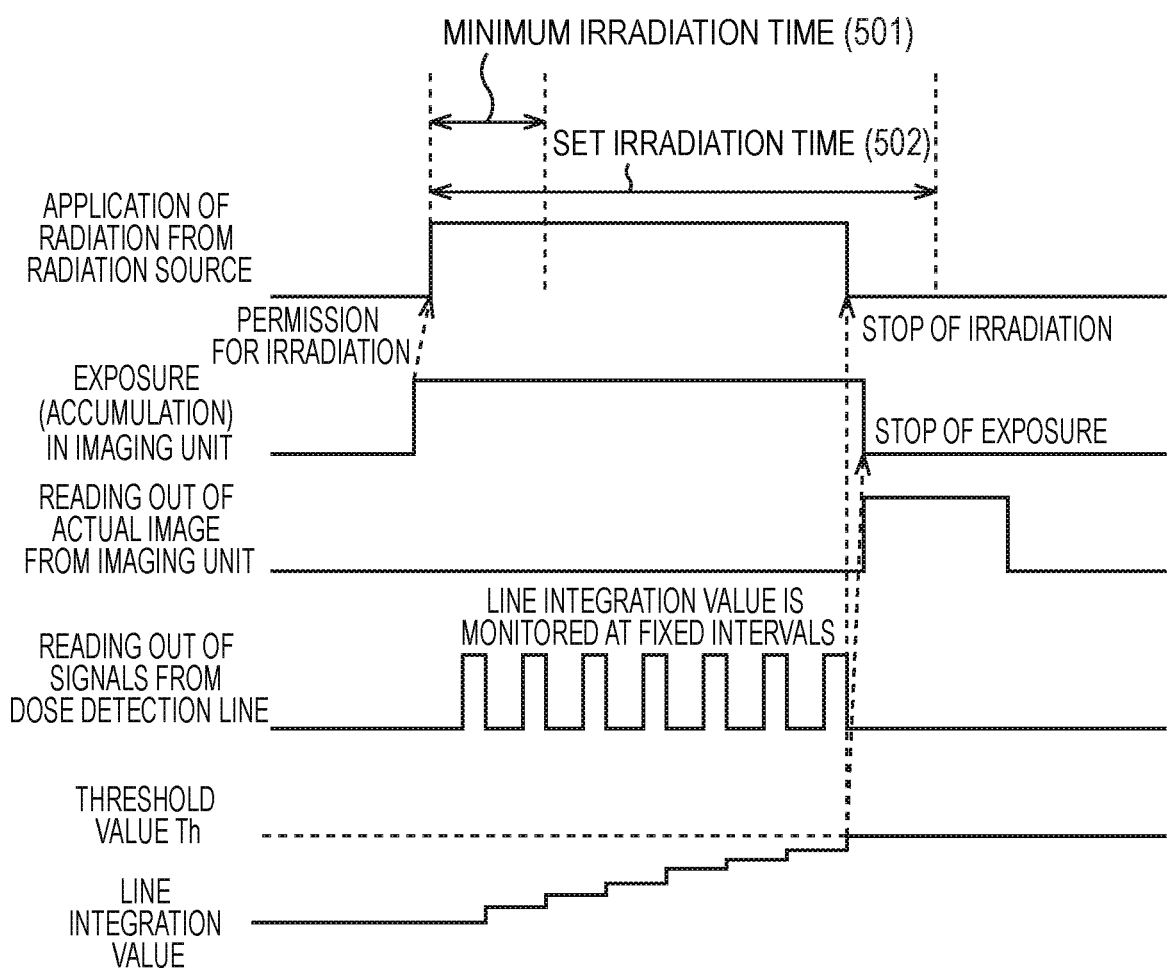
FIG. 5 is a timing chart for illustrating an example of a first processing procedure involved in a method of controlling a radiation imaging system including a radiation imaging apparatus according to a second embodiment of the present invention.

FIG. 5 is a timing chart for illustrating an example of a first processing procedure involved in a method of controlling the radiation imaging system 10 including the radiation imaging apparatus 100 according to the second embodiment of the present invention. In FIG. 5, the same name is assigned to the same component as that illustrated in FIG. 3, and a detailed description thereof is omitted.

In the timing chart illustrated in FIG. 5, as illustrated in FIG. 5, there is illustrated an example of a processing procedure to be performed after the "permission for irradiation" with the radiation 301 is issued in Step S104 of FIG. 4. Specifically, when the permission instruction information for permitting the irradiation of the radiation 301 from the radiation source 300 is transmitted from the processing unit 130 to the irradiation control unit 200, the irradiation control unit 200 starts the irradiation of the radiation 301 from the radiation source 300. It is assumed that, in the second embodiment, the irradiation control unit 200 sets, as a period of time for performing irradiation of the radiation 301 from the radiation source 300, a minimum irradiation time 501 and a set irradiation time 502 relating to radiation imaging of the subject H to be examined.

At the time of start of the irradiation of the radiation 301 from the radiation source 300, in each pixel 210 of the pixel region 121 of the imaging unit 120, exposure of accumulating electric charges is started. Then, the processing unit 130 reads out, for example, electric signals (dose signals) at fixed time intervals from the dose detection line (dose signal output pixel line) including one or a plurality of rows of the pixels 210 of the pixel region 121. At this time, every time the electric signals (dose signals) are read out from the dose detection line (dose signal output pixel line), the exposure is performed and the electric charges are reset, and hence the processing unit 130 integrates the read electric signals (dose signals) of the dose detection line (dose signal output pixel line) to calculate an integration value. The integration value obtained by integrating the electric signals (dose signals) of the dose detection line (dose signal output pixel line) is hereinafter referred to as "line integration value".

Then, during the period in which the radiation 301 is being applied to the imaging unit 120 based on the transmitted permission instruction information, the processing unit 130 performs, at fixed time intervals, processing of comparing the line integration value to the threshold value Th. Then, in the example illustrated in FIG. 5, when the line integration value exceeds the threshold value Th, the processing unit 130 transmits stop instruction information for stopping the irradiation of the radiation 301 to the imaging unit 120 to, for example, the irradiation control unit 200 and the computer 110. When receiving the stop instruction information from the processing unit 130, the irradiation control unit 200 transmits the irradiation stop instruction to the radiation source 300 to stop the irradiation of the radiation 301 from the radiation source 300. Further, when receiving the stop instruction information from the processing unit 130, the computer 110 stops the exposure operation in each pixel 210 of the pixel region 121 of the imaging unit 120. Subsequently, the computer 110 performs an operation of reading out electric signals (image signals) of each pixel 210 (which may include the pixel caused to function as the pixel of the dose detection line (dose signal output pixel)) that have been accumulated so far.

As illustrated in FIG. 5, appropriate radiation stop control can be performed by stopping the irradiation of the radiation 301 to the imaging unit 120 when the line integration value exceeds the threshold value Th. With this configuration, it is possible to perform appropriate automatic exposure control (AEC).

Now, the threshold value Th to be set for the processing unit 130 is described. A different value can be set as the threshold value Th depending on a site of the subject H to be examined. For example, when a region to be imaged is a site containing a large volume of air, for example, a lung region of the subject H to be examined, such a site tends to easily transmit the radiation 301, and hence a large dose of the radiation 301 reaches the pixel region 121. Accordingly, the threshold value Th to be set for such a site is a high value. In contrast, when a region to be imaged is a site that does not easily transmit the radiation 301, for example, a bone or an organ of the subject H to be examined, the threshold value Th to be set for such a site is a low value.

Further, in the example illustrated in FIG. 5, in a period equal to or longer than the minimum irradiation time 501 and within the set irradiation time 502 selected by, for example, a radiology technician depending on an imaging technique, appropriate radiation stop control using the above-mentioned threshold value Th is performed.

Figure 6:
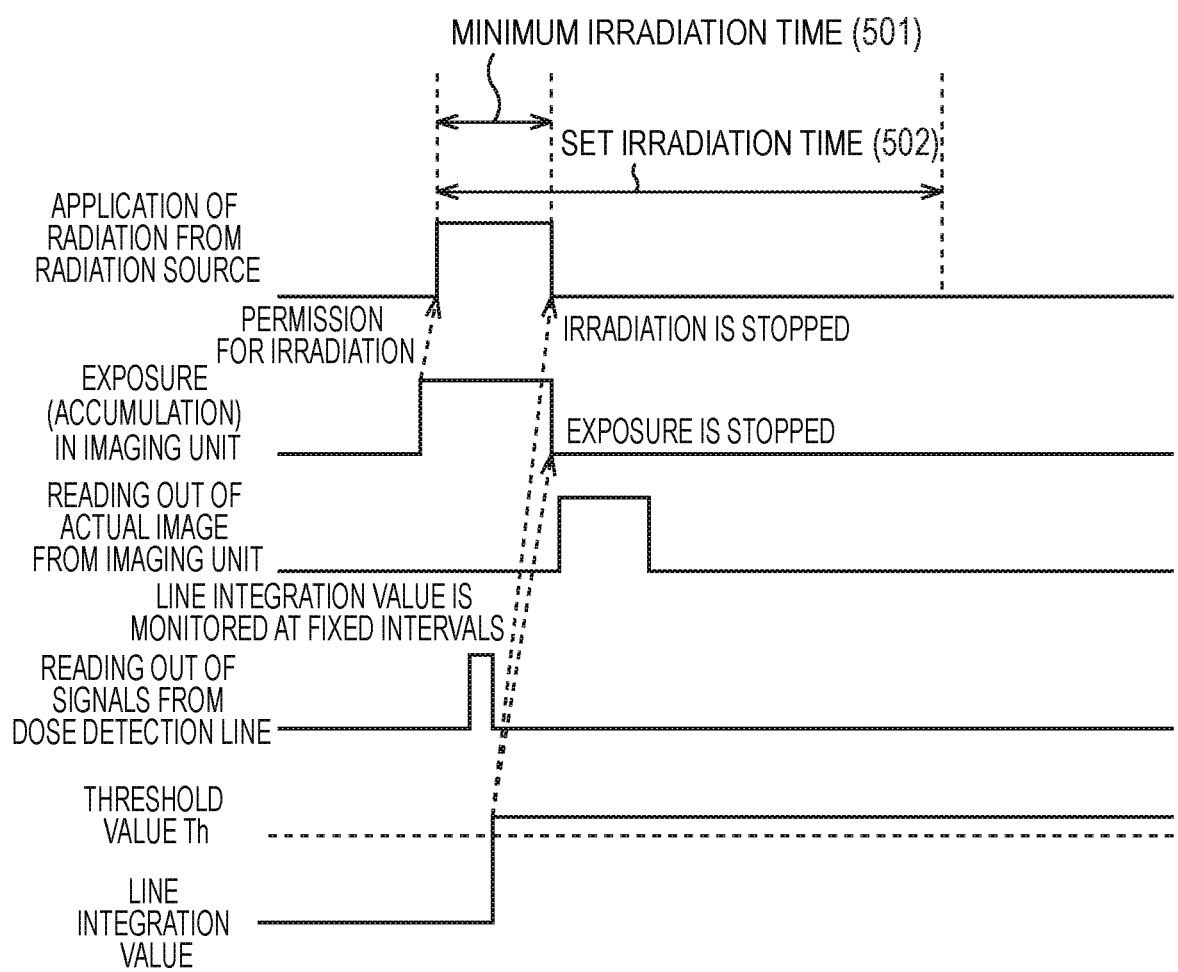
FIG. 6 is a timing chart for illustrating an example of a second processing procedure included in the method of controlling the radiation imaging system including the radiation imaging apparatus according to the second embodiment.

FIG. 6 is a timing chart for illustrating an example of a second processing procedure involved in a method of controlling the radiation imaging system 10 including the radiation imaging apparatus 100 according to the second embodiment of the present invention. In FIG. 6, the same name is assigned to the same component as those illustrated in FIG. 3 and FIG. 5, and a detailed description thereof is omitted.

In the timing chart illustrated in FIG. 6, in the same manner as in FIG. 5 described above, there is illustrated an example of a processing procedure to be performed after the "permission for irradiation" with the radiation 301 is issued in Step S104 of FIG. 4.

In FIG. 6, in the case where the line integration value exceeds the threshold value Th within the period of the minimum irradiation time 501 of the radiation 301, when the minimum irradiation time 501 has elapsed, the processing unit 130 transmits stop instruction information for stopping the irradiation of the radiation 301 to the imaging unit 120 to, for example, the irradiation control unit 200 and the computer 110. This is because, in FIG. 6, although the above-mentioned line integration value exceeds the threshold value Th in a period of time shorter than the set minimum irradiation time 501, the radiation source 300 is controlled by the irradiation control unit 200, and hence the radiation 301 applied from the radiation source 300 cannot be stopped. Accordingly, in FIG. 6, when the minimum irradiation time 501 has elapsed, the radiation stop control is performed, and further, the operation of stopping the exposure operation in each pixel 210 of the pixel region 121 of the imaging unit 120 and then reading out the electric signal (image signal) from each pixel 210 is performed. At this time, in the computer 110, radiation image data generated based on the read image signals may be subjected to image correction of decreasing the gain of the image data in a period of time from a time at which the above-mentioned line integration value has exceeded the threshold value Th to a time at which the irradiation of the radiation is stopped.

Further, the dose of the radiation 301 is expressed as a product of a tube current of the radiation source 300 and the irradiation time. Accordingly, for example, a proper set value of the tube current may be calculated based on whether or not there is stop instruction information within the minimum irradiation time 501, a time at which the above-mentioned line integration value has exceeded the threshold value Th, and a tube current that is currently set so that the irradiation time is equal to or longer than the minimum irradiation time 501. Then, the calculated set value may be displayed on the display 150. It should be noted, however, that the value of the tube current to be set varies depending on, in addition to those factors, a tube voltage of the radiation source 300, the distance between the radiation source 300 and the subject H to be examined, and whether or not there is a grid, and hence a specific numerical value of the tube current is not given herein.

Figure 7:
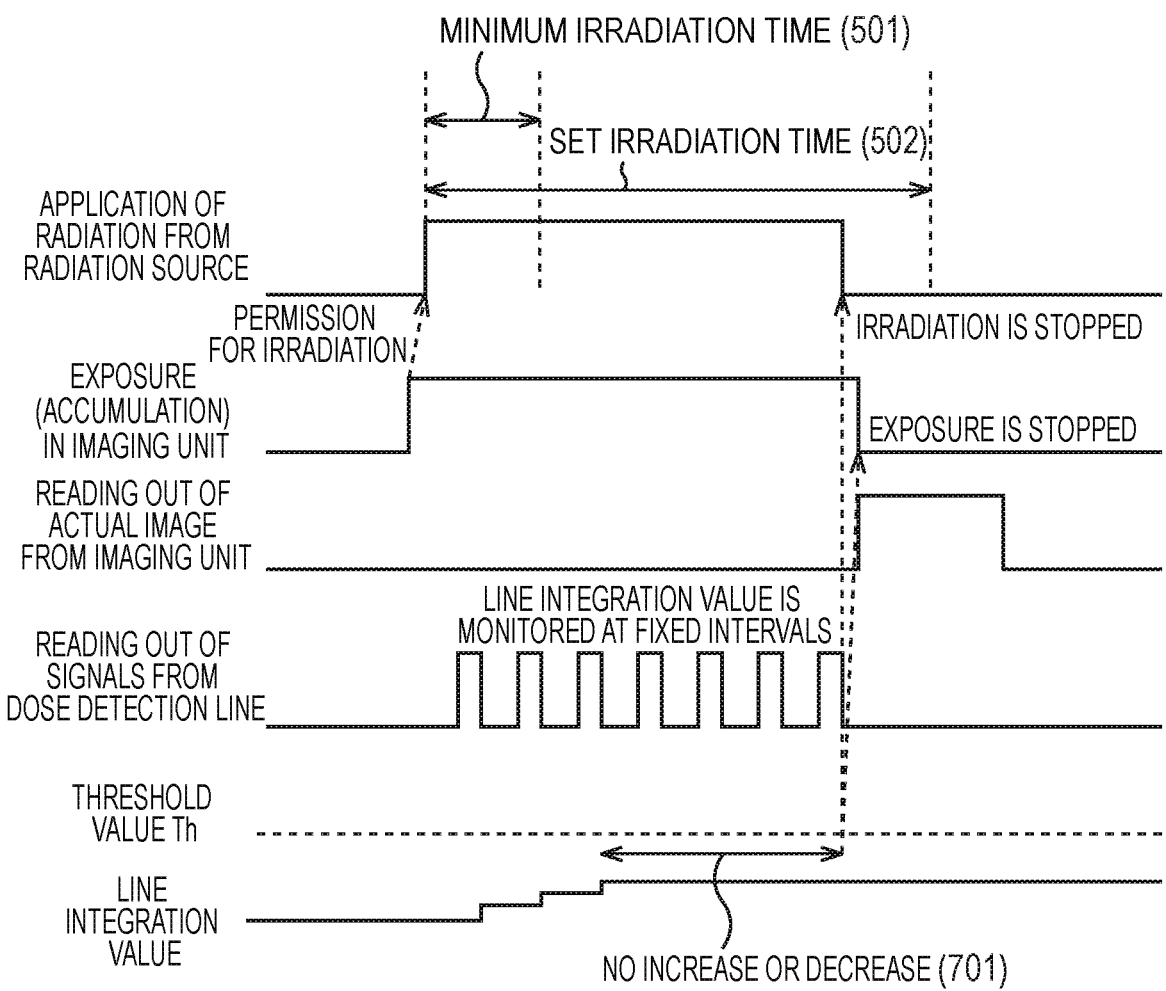
FIG. 7 is a timing chart for illustrating an example of a third processing procedure included in the method of controlling the radiation imaging system including the radiation imaging apparatus according to the second embodiment.

FIG. 7 is a timing chart for illustrating an example of a third processing procedure involved in a method of controlling the radiation imaging system 10 including the radiation imaging apparatus 100 according to the second embodiment of the present invention. In FIG. 7, the same name is assigned to the same component as those illustrated in FIG. 3, FIG. 5, and FIG. 6, and a detailed description thereof is omitted.

In the timing chart illustrated in FIG. 7, in the same manner as in FIG. 5 described above, there is illustrated an example of a processing procedure to be performed after the "permission for irradiation" with the radiation 301 is issued in Step S104 of FIG. 4.

In FIG. 7, after the minimum irradiation time 501 of the radiation 301 has elapsed, in the case where the line integration value does not exceed the threshold value Th and the line integration value does not increase or decrease by a predetermined amount or more within a fixed period 701, when the fixed period 701 has elapsed, the processing unit 130 transmits stop instruction information for stopping the irradiation of the radiation 301 to the imaging unit 120 to, for example, the irradiation control unit 200 and the computer 110. Specifically, in FIG. 7, in addition to the determination of whether the above-mentioned line integration value exceeds the threshold value Th, the increase and decrease (variation) of the above-mentioned line integration value are also monitored.

In the example illustrated in FIG. 7, in the case where the line integration value does not increase or decrease by the predetermined amount or more within the fixed period 701, even when the line integration value does not exceed the set threshold value Th, the processing unit 130 transmits the stop instruction information for stopping the irradiation of the radiation 301 to the irradiation control unit 200 and the computer 110. As a result, when the fixed period 701 has elapsed, the irradiation of the radiation 301 from the radiation source 300 is stopped, and further, the operation of stopping the exposure operation in each pixel 210 of the pixel region 121 of the imaging unit 120 and then reading out the electric signal (image signal) from each pixel 210 is performed.

In the processing illustrated in FIG. 7, in which when the line integration value does not increase or decrease by the predetermined amount or more within the fixed period 701, the irradiation of the radiation 301 is stopped at the time of the line integration value being equal to or smaller than the set threshold value Th, radiation image data may have a level lower than an expected threshold value because, for example, a site of the subject H to be examined includes a material that does not easily transmit the radiation 301. However, by monitoring the line integration value as well, it is possible to prevent the subject H to be examined from being improperly exposed to the radiation 301 without continuation of the irradiation of the radiation 301.

Figure 8:
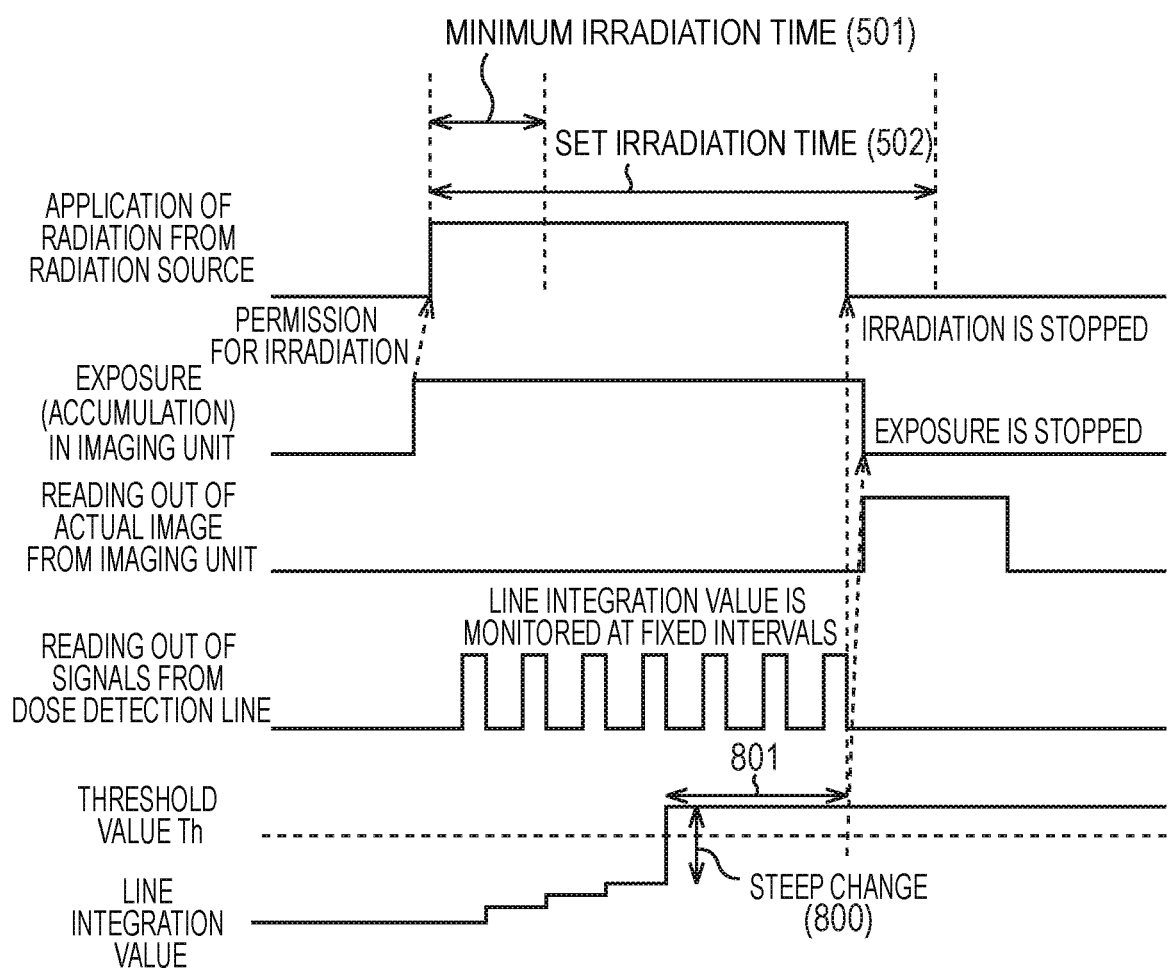
FIG. 8 is a timing chart for illustrating an example of a fourth processing procedure included in the method of controlling the radiation imaging system including the radiation imaging apparatus according to the second embodiment.

FIG. 8 is a timing chart for illustrating an example of a fourth processing procedure involved in a method of controlling the radiation imaging system 10 including the radiation imaging apparatus 100 according to the second embodiment of the present invention. In FIG. 8, the same name is assigned to the same component as those illustrated in FIG. 3, FIG. 5 to FIG. 7, and a detailed description thereof is omitted.

In the timing chart illustrated in FIG. 8, in the same manner as in FIG. 5 described above, there is illustrated an example of a processing procedure to be performed after the "permission for irradiation" with the radiation 301 is issued in Step S104 of FIG. 4.

In FIG. 8, after the minimum irradiation time 501 of the radiation 301 has elapsed, in the case where the line integration value exhibits an increase or decrease (steep change) 800 by a predetermined amount or more within a fixed period 801, when the fixed period 801 has elapsed, the processing unit 130 transmits stop instruction information for stopping the irradiation of the radiation 301 to the imaging unit 120 to, for example, the irradiation control unit 200 and the computer 110. Specifically, in FIG. 8, in addition to the determination of whether the above-mentioned line integration value exceeds the threshold value Th, the increase and decrease (variation) 800 of the above-mentioned line integration value are also monitored.

In the example illustrated in FIG. 8, in the case where the line integration value exhibits the increase or decrease (steep change) 800 by the predetermined amount or more within the fixed period 801, the processing unit 130 transmits the stop instruction information for stopping the irradiation of the radiation 301 to the irradiation control unit 200 and the computer 110. As a result, when the fixed period 801 has elapsed, the irradiation of the radiation 301 from the radiation source 300 is stopped, and further, the operation of stopping the exposure operation in each pixel 210 of the pixel region 121 of the imaging unit 120 and then reading out the electric signal (image signal) from each pixel 210 is performed.

As illustrated in FIG. 8, when the line integration value exhibits the increase or decrease (steep change) 800 by the predetermined amount or more within the fixed period 801, the control to stop the irradiation of the radiation 301 is performed because trouble occurs in the dose signal output pixel, or because trouble with the control of the irradiation of the radiation 301 is expected, for example. That is, there is a possibility that it is not desired to continue the radiation imaging without stopping the radiation imaging. Accordingly, for example, as illustrated in FIG. 8, when the line integration value exhibits the increase or decrease (steep change) 800 by the predetermined amount or more within the fixed period 801, alert indicating the steep change may be displayed on the display 150 to alert the user to the change.

Figure 9:
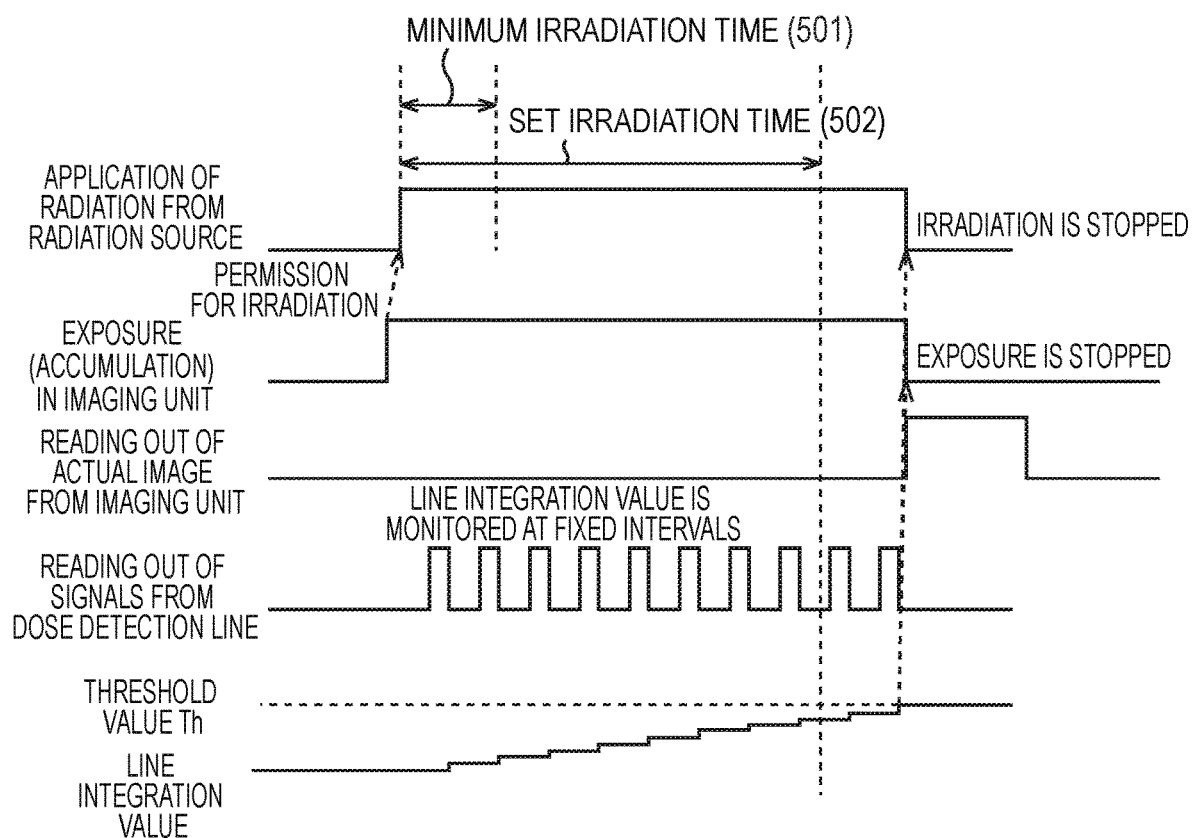
FIG. 9 is a timing chart for illustrating an example of a fifth processing procedure included in the method of controlling the radiation imaging system including the radiation imaging apparatus according to the second embodiment.

FIG. 9 is a timing chart for illustrating an example of a fifth processing procedure involved in a method of controlling the radiation imaging system 10 including the radiation imaging apparatus 100 according to the second embodiment of the present invention. In FIG. 9, the same name is assigned to the same component as those illustrated in FIG. 3 and FIG. 5 to FIG. 8, and a detailed description thereof is omitted.

In the timing chart illustrated in FIG. 9, in the same manner as in FIG. 5 described above, there is illustrated an example of a processing procedure to be performed after the "permission for irradiation" with the radiation 301 is issued in Step S104 of FIG. 4.

In FIG. 9, when the line integration value does not exceed the threshold value Th until the set irradiation time 502 of the radiation 301 elapses, and the line integration value continues to increase within a predetermined range, the processing unit 130 transmits continuation instruction information for continuing the irradiation of the radiation 301 to the imaging unit 120 until the line integration value exceeds the threshold value Th to, for example, the irradiation control unit 200 and the computer 110. Specifically, in FIG. 9, in addition to the determination of whether the above-mentioned line integration value exceeds the threshold value Th, the increase and decrease (variation) of the line integration value are also monitored.

In the example illustrated in FIG. 9, the line integration value exhibits an increase corresponding to a dose of applied radiation per unit time, but when the line integration value does not reach the threshold value Th even after the set irradiation time 502 has elapsed, the irradiation of the radiation 301 is continued even after the set irradiation time 502 has elapsed. Then, in the example illustrated in FIG. 9, after the set irradiation time 502 has elapsed, when the line integration value has reached the threshold value Th, the processing unit 130 transmits, at this time, stop instruction information for stopping the irradiation of the radiation 301 to the irradiation control unit 200 and the computer 110. As a result, when the line integration value has reached the threshold value Th, the irradiation of the radiation 301 from the radiation source 300 is stopped, and further, the operation of stopping the exposure operation in each pixel 210 of the pixel region 121 of the imaging unit 120 and then reading out the electric signal (image signal) from each pixel 210 is performed.

In the example illustrated in FIG. 9, even after the set irradiation time 502 has elapsed, the irradiation of the radiation 301 is continued to perform a proper exposure operation for each pixel 210 of the pixel region 121. Further, in the example illustrated in FIG. 9, after the radiation imaging, the difference between the set irradiation time 502 and a period of time for which the radiation 301 has actually been applied may be displayed on the display 150. When the period of time for which the radiation 301 has actually been applied becomes longer, that is, the imaging time becomes longer, obtained radiation image data may be unsharp due to vibrations or shakes of the subject H to be examined. Accordingly, for example, a proper tube current set value of the radiation source 300 may be displayed on the display 150 so as to allow the user to utilize the value for the next radiation imaging.

Figure 10:
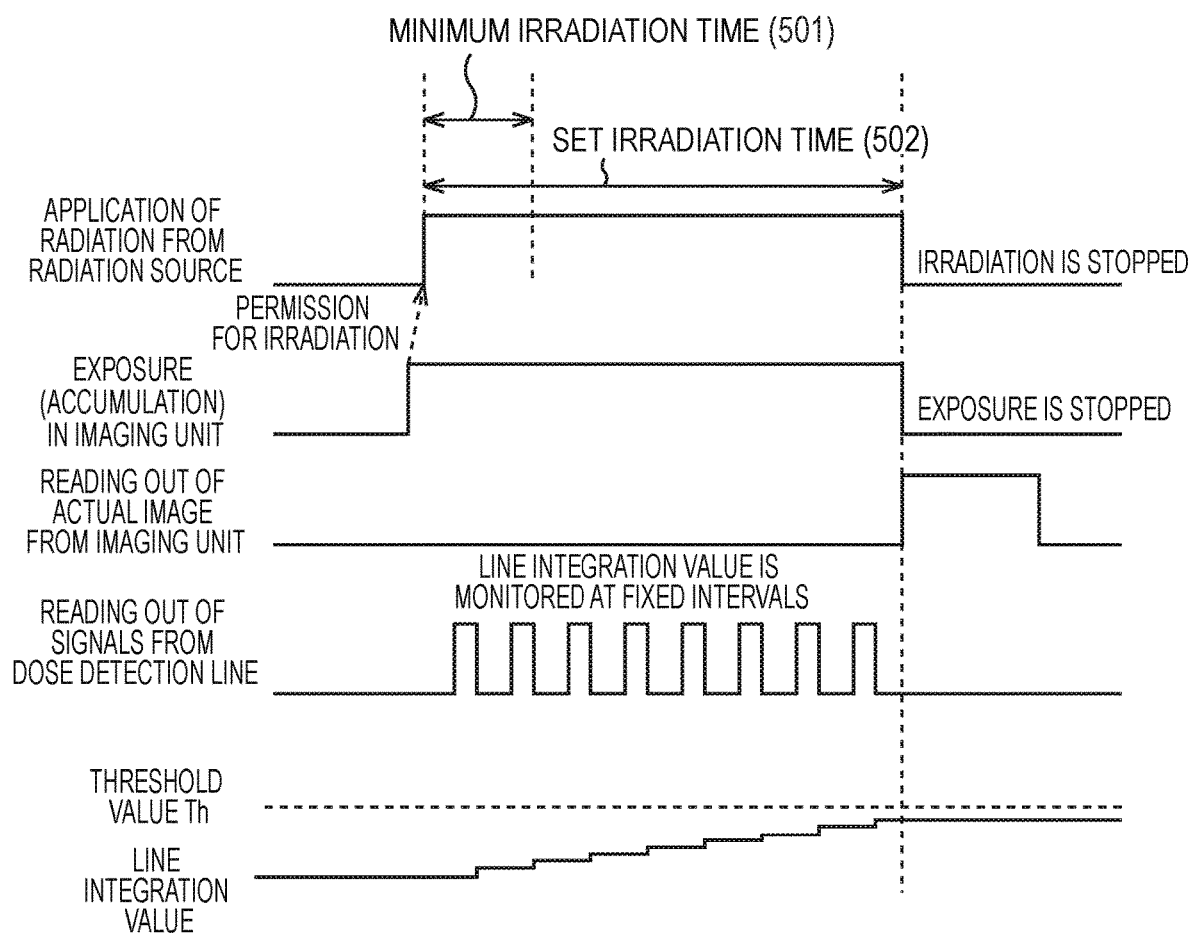
FIG. 10 is a timing chart for illustrating an example of a sixth processing procedure included in the method of controlling the radiation imaging system including the radiation imaging apparatus according to the second embodiment.

FIG. 10 is a timing chart for illustrating an example of a sixth processing procedure included in the method of controlling the radiation imaging system 10 including the radiation imaging apparatus 100 according to the second embodiment of the present invention. In FIG. 10, the same name is assigned to the same component as those illustrated in FIG. 3 and FIG. 5 to FIG. 9, and a detailed description thereof is omitted.

In the timing chart illustrated in FIG. 10, in the same manner as in FIG. 5 described above, there is illustrated an example of a processing procedure to be performed after the "permission for irradiation" with the radiation 301 is issued in Step S104 of FIG. 4.

In FIG. 10, in the case where the line integration value does not exceed the threshold value Th until the set irradiation time 502 of the radiation 301 elapses, when the set irradiation time 502 has elapsed, the processing unit 130 transmits the stop instruction information for stopping the irradiation of the radiation 301 to the imaging unit 120 to, for example, the irradiation control unit 200 and the computer 110. As a result, when the set irradiation time 502 has elapsed, the irradiation of the radiation 301 from the radiation source 300 is stopped, and further, the operation of stopping the exposure operation in each pixel 210 of the pixel region 121 of the imaging unit 120 and then reading out the electric signal (image signal) from each pixel 210 is performed. Then, in the example illustrated in FIG. 10, the line integration value does not exceed the threshold value Th until the set irradiation time 502 of the radiation 301 elapses, and hence the computer 110 corrects the gain of the obtained radiation image data. Further, when the gain correction is performed after the radiation imaging, a corrected sensitivity or dB may be displayed on the display 150.

As illustrated in FIG. 10, the irradiation of the radiation 301 is restricted at the time of elapse of the set irradiation time 502 when, for example, it is desired to restrict the amount of exposure of the radiation 301 to the subject H to be examined.

Further, in the second embodiment described with reference to FIG. 5 to FIG. 10, for example, a predetermined tube current set value of the radiation source 300, which is calculated based on an actual irradiation time relating to the irradiation of the radiation 301, may be displayed on the display 150.

According to the second embodiment described above, it is possible to perform appropriate radiation stop control in addition to the effects of the first embodiment described above.

Third Embodiment

Next, a third embodiment of the present invention is described. In the following description of the third embodiment, a description of matters common to the first and second embodiments described above is omitted, and matters different from those of the first and second embodiments described above are described.

A schematic configuration of a radiation imaging system including a radiation imaging apparatus according to the third embodiment is the same as the schematic configuration of the radiation imaging system 10 of the radiation imaging apparatus 100 according to the first embodiment, which is illustrated in FIG. 0.1.

Figure 11:
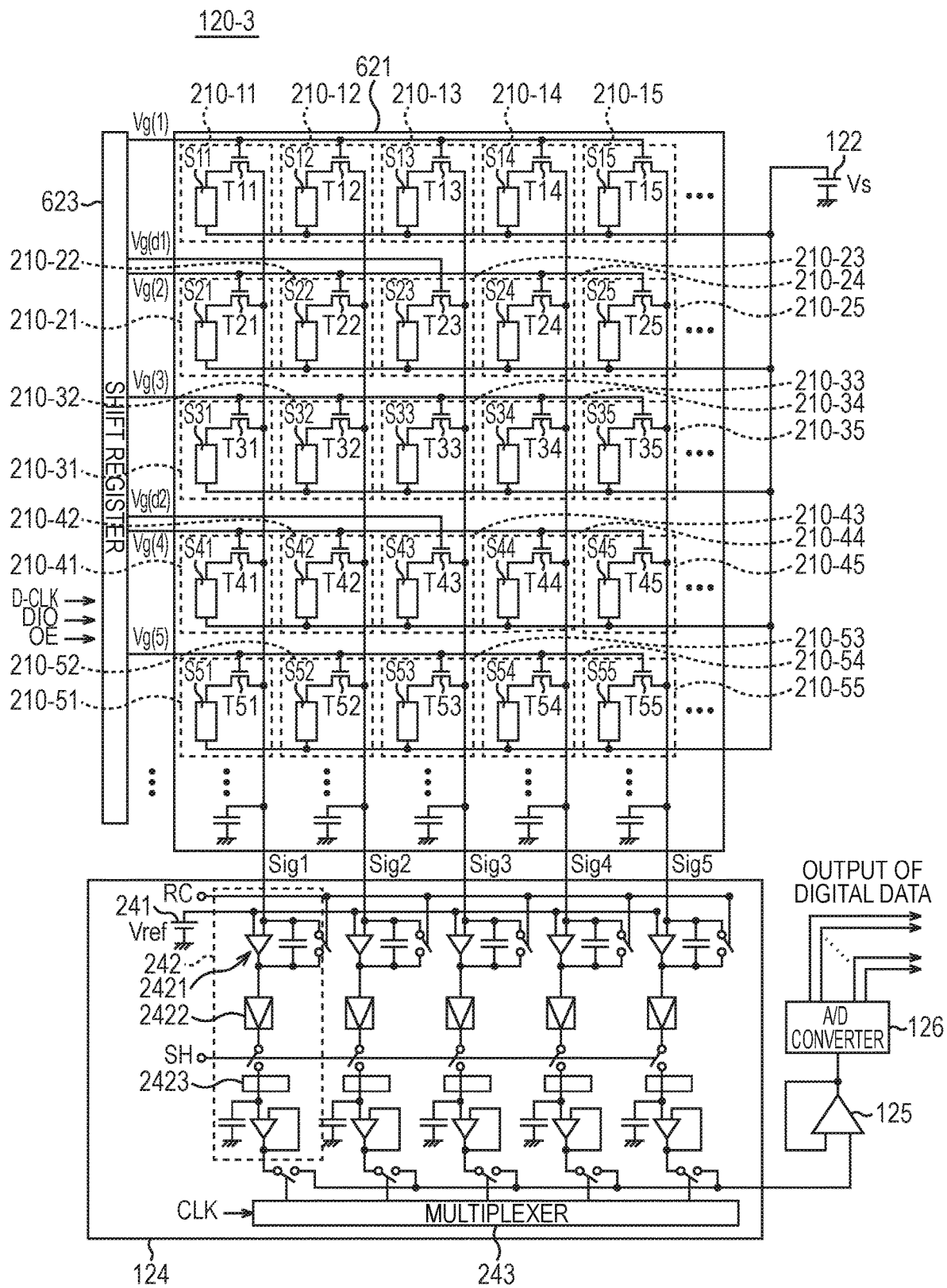
FIG. 11 is an illustration of a third embodiment of the present invention, and is a diagram for illustrating another example of the internal configuration of the imaging unit illustrated in FIG. 1.

FIG. 11 is an illustration of the third embodiment of the present invention, and is a diagram for illustrating an example of the internal configuration of the imaging unit 120 illustrated in FIG. 1. The imaging unit 120 in the third embodiment illustrated in FIG. 11 is hereinafter referred to as "imaging unit 120-3". Further, in FIG. 11, the same reference numeral is assigned to the same component as that illustrated in FIG. 2, and a detailed description thereof is omitted.

As illustrated in FIG. 11, the imaging unit 120-3 includes a pixel region 621, the bias power supply 122, a shift register 623 being the drive circuit, the readout circuit 124, the buffer amplifier 125, and the A/D converter 126.

In the first and second embodiments described above, as illustrated in FIG. 2, there is adopted the mode in which the timing to drive each pixel 210 is varied from one to another to cause the same pixel 210 as one of the dose signal output pixel and the image signal output pixel. In contrast, in the third embodiment, there is adopted a mode in which the dose signal output pixel and the image signal output pixel are formed as different pixels in the pixel region 621 illustrated in FIG. 11.

In FIG. 11, of the plurality of pixels 210 arranged in the pixel region 621, a pixel 210-23 connected to a drive wiring Vg(d1) and a pixel 210-43 connected to a drive wiring Vg(d2) are the dose signal output pixels. Further, of the plurality of pixels 210 arranged in the pixel region 621, the pixels 210 connected to drive wirings Vg(1) to Vg(5) are the image signal output pixels.

When the third embodiment is applied to the first embodiment, during the period in which the radiation 301 is not applied to the imaging unit 120-3 from the radiation source 300, the processing unit 130 performs processing of comparing, for example, an integration value of electric signals (dose signals) output from the dose signal output pixels 210-23 and 210-43 of the imaging unit 120-3 to the threshold value Th. After that, in the third embodiment, when the above-mentioned integration value exceeds the threshold value Th, the processing unit 130 transmits to the irradiation control unit 200 the prohibition instruction information for prohibiting the irradiation of the radiation 301 from the radiation source 300 to the imaging unit 120-3. Then, when receiving the prohibition instruction information from the processing unit 130, the irradiation control unit 200 transmits the irradiation prohibition instruction to the radiation source 300 to control the radiation source 300 so as to prevent the radiation 301 from being applied from the radiation source 300. Meanwhile, in the third embodiment, when the above-mentioned integration value does not exceed the threshold value Th, the processing unit 130 transmits to the irradiation control unit 200 the permission instruction information for permitting the irradiation of the radiation 301 from the radiation source 300 to the imaging unit 120-3. Then, when receiving the permission instruction information from the processing unit 130, the irradiation control unit 200 transmits the irradiation permission instruction to the radiation source 300 to control the radiation source 300 such that the radiation 301 is applied from the radiation source 300.

Further, when the third embodiment is applied to the second embodiment, during the period in which the radiation 301 is being applied to the imaging unit 120-3 based on the transmitted permission instruction information, the processing unit 130 performs, at fixed time intervals, processing of comparing, for example, an integration value of electric signals (dose signals) output from the dose signal output pixels 210-23 and 210-43 of the imaging unit 120-3 to the threshold value Th. Further, when the third embodiment is applied to the second embodiment described with reference to FIG. 5 to FIG. 10, in place of the line integration value in the second embodiment, the integration value of the electric signals (dose signals) output from the dose signal output pixels 210-23 and 210-43 may be applied.

Further, in the example illustrated in FIG. 11, one dose signal output pixel 210 is connected to each of the drive wiring Vg(d1) and the drive wiring Vg(d2), but a plurality of dose signal output pixels 210 may be connected to each of the drive wiring Vg(d1) and the drive wiring Vg(d2).

Further, in the example illustrated in FIG. 11, the shift register 623 is configured to drive, via the drive wirings Vg(1) to Vg(5) and the drive wirings Vg(d1) and Vg(d2), the pixels 210 connected to the drive wirings at different drive timings.

Also in the third embodiment, in the same manner as in the first embodiment described above, it is possible to prevent inappropriate radiation stop control from being performed. Moreover, also in the third embodiment, in the same manner as in the second embodiment described above, it is possible to perform appropriate radiation stop control.

According to the first to third embodiments of the present invention described above, it is possible to prevent inappropriate radiation stop control from being performed.

Other Embodiments

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

The present invention can be implemented in various forms without departing from the technical ideas or the main features thereof. While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2019-118381, filed Jun. 26, 2019 which is hereby incorporated by reference herein in its entirety.

What is claimed is:

1. A radiation imaging apparatus configured to perform imaging by radiation, the radiation imaging apparatus comprising:
   an imaging unit including a dose signal output pixel arranged to output an electric signal based on a dose of the radiation that has entered the dose signal output pixel; and
   a processing unit configured to perform processing of comparing an integration value of the electric signal output from the dose signal output pixel to a threshold value during a period in which the radiation is not irradiated to the imaging unit.

2. The radiation imaging apparatus according to claim 1, wherein the processing unit is configured to issue a prohibition instruction for prohibiting irradiation of the radiation to the imaging unit if the integration value exceeds the threshold value.

3. The radiation imaging apparatus according to claim 2 further comprising a display configured to display alert if the prohibition instruction is issued from the processing unit.

4. The radiation imaging apparatus according to claim 1, wherein the processing unit is configured to issue a permission instruction for permitting the irradiation of the radiation to the imaging unit if the integration value does not exceed the threshold value.

5. The radiation imaging apparatus according to claim 4, wherein the processing unit is configured to perform processing of further comparing the integration value of the electric signal output from the dose signal output pixel to the threshold value during a period in which the radiation is irradiated to the imaging unit based on the permission instruction.

6. The radiation imaging apparatus according to claim 5, wherein the processing unit is configured to issue a stop instruction to stop the irradiation of the radiation to the imaging unit if the integration value exceeds the threshold value.

7. The radiation imaging apparatus according to claim 5, wherein the processing unit is configured to issue a stop instruction to stop the irradiation of the radiation to the imaging unit when the minimum irradiation time has elapsed if the integration value exceeds the threshold value during a period of a minimum irradiation time of the radiation.

8. The radiation imaging apparatus according to claim 5, wherein the processing unit is configured to issue a stop instruction to stop the irradiation of the radiation to the imaging unit if, after a minimum irradiation time of the radiation has elapsed, the integration value does not exceed the threshold value and the integration value does not increase or decrease by a predetermined amount or more within a fixed period.

9. The radiation imaging apparatus according to claim 5, wherein the processing unit is configured to issue a stop instruction to stop the irradiation of the radiation to the imaging unit if, after a minimum irradiation time of the radiation has elapsed, the integration value has increased or decreased by a predetermined amount or more within a fixed period.

10. The radiation imaging apparatus according to claim 5, wherein the processing unit is configured to issue a continuation instruction to continue the application of the radiation to the imaging unit until the integration value exceeds the threshold value if the integration value does not exceed the threshold value until a set irradiation time of the radiation elapses and the integration value continues to increase within a predetermined range.

11. The radiation imaging apparatus according to claim 5, wherein the processing unit is configured to issue a stop instruction to stop the application of the radiation to the imaging unit when the set irradiation time has elapsed if the integration value does not exceed the threshold value until a set irradiation time of the radiation elapses.

12. The radiation imaging apparatus according to claim 1, wherein the imaging unit includes the plurality of dose signal output pixels and a plurality of image signal output pixels each arranged to output an image signal relating to a radiation image, and
   wherein the processing unit is configured to use, as the integration value, an integration value of electric signals output from the plurality of dose signal output pixels.

13. A radiation imaging system comprising:
   the radiation imaging apparatus of claim 1;
   a radiation source arranged to perform irradiation; and
   an irradiation control unit configured to control the irradiation by the radiation source.

14. The radiation imaging system according to claim 13, wherein the radiation imaging apparatus includes a display configured to display a predetermined tube current set value of the radiation source, which is calculated based on an actual irradiation time relating to the application of the radiation.

15. A method of controlling a radiation imaging apparatus, the radiation imaging apparatus including an imaging unit, which includes a dose signal output pixel arranged to output an electric signal based on a dose of a radiation that has entered the dose signal output pixel, and the radiation imaging apparatus being configured to perform imaging by the radiation, the method comprising performing processing of comparing an integration value of the electric signal output from the dose signal output pixel to a threshold value during a period in which the radiation is not applied to the imaging unit.

16. A radiation imaging apparatus configured to perform imaging by radiation, the radiation imaging apparatus comprising:

an imaging unit including a dose signal output pixel arranged to output an electric signal based on a dose of the radiation that has entered the dose signal output pixel; and a processing unit configured to perform processing of comparing an integration value of the electric signal output from the dose signal output pixel to a threshold value, wherein the processing unit is configured to issue a stop instruction to stop the irradiation of the radiation to the imaging unit if, after a minimum irradiation time of the radiation has elapsed, the integration value does not exceed the threshold value and the integration value does not increase by a predetermined amount or more within a fixed period.

17. The radiation imaging apparatus according to claim 16, wherein the imaging unit includes the plurality of dose signal output pixels, and wherein the processing unit is configured to use, as the integration value, an integration value of electric signals output from the plurality of dose signal output pixels.

18. A radiation imaging system comprising:

the radiation imaging apparatus of claim 16;

a radiation source arranged to perform irradiation; and an irradiation controller configured to control the irradiation by the radiation source.

19. The radiation imaging system according to claim 18, wherein the radiation imaging apparatus includes a display configured to display a predetermined tube current set value of the radiation source, which is calculated based on an actual irradiation time relating to the application of the radiation.

* * * * *